United States Patent [19]

Cummins

[11] 4,336,907

[45] Jun. 29, 1982

[54] APPARATUS FOR SUPPLYING CORROSION INHIBITING MATERIAL TO INACCESSIBLE METAL SURFACES

[76] Inventor: Richard D. Cummins, 6092 Emerson Dr., Orchard Park, N.Y. 14127

[21] Appl. No.: 213,812

[22] Filed: Dec. 8, 1980

[51] Int. Cl.[3] .......... A61L 9/04

[52] U.S. Cl. .......... 239/57; 239/309; 239/600

[58] Field of Search .......... 239/34, 53-57, 239/60, 309, 600; 222/83, 180; 411/38

[56] References Cited

U.S. PATENT DOCUMENTS

| | | | |
|---|---|---|---|
| 1,760,598 | 5/1930 | Horn | 239/57 |
| 1,769,593 | 7/1930 | Mercogliano | 239/57 |
| 1,931,132 | 10/1933 | Hinckley | 239/57 |
| 2,500,169 | 3/1950 | Ellis . | |
| 2,559,281 | 7/1951 | Croessant | 411/38 |
| 2,577,219 | 12/1951 | Wachter et al. . | |
| 2,592,451 | 4/1952 | Moore et al. . | |
| 2,766,069 | 10/1956 | Tennyson . | |
| 2,857,005 | 10/1958 | Medlock . | |
| 3,871,823 | 3/1975 | Skildum . | |
| 3,904,123 | 9/1975 | Fils . | |
| 3,999,543 | 12/1976 | Lacey . | |
| 4,106,701 | 8/1978 | Siefken . | |
| 4,108,382 | 8/1978 | Ryd et al. . | |
| 4,161,284 | 7/1979 | Rattan . | |

*Primary Examiner*—Bruce H. Stoner, Jr.
*Assistant Examiner*—Michael J. Forman
*Attorney, Agent, or Firm*—Bean, Kauffman & Bean

[57] ABSTRACT

A cup-shaped retainer is provided with a side wall having a mounting rim portion joined to one end thereof and a bottom wall joined to an opposite end of the side wall and having a mounting aperture sized to threadably receive a mounting screw. The side wall of the retainer is externally sized to permit insertion thereof inwardly through an access opening formed in a vehicle body or door panel or the like and the retainer is interiorly sized to removably receive a disposable cartridge filled with a corrosion inhibiting material. The mounting screw is fitted with a sealing disc or cover and may be inserted successively through the cartridge and the mounting aperture to puncture the cartridge to permit escape of its contents, to clamp the sealing disc in surface engagement with the outer surface of the vehicle body panel peripherally bounding the access opening and to effect deformation of the mounting rim portion of the retainer into clamping engagement with the vehicle body panel peripherally of the aperture.

7 Claims, 3 Drawing Figures

12b
12
12a
12c
14
10
20
30
34
32
32c
32d
38
38a
38b
40
22
22a
22b
22c
28
28c
28d
26
26a
26b
26c
44

10
12
12a
12b
12c
14
20
22
22a
22b
22c
24
26
26a
26b
28
28a
28b
28c
28d
30
32
34
36
38
38a
38b
38c
38d
40
44

10
12
12a
12b
14
20
22
22a
22b
22c
24
26
26a
26c
28
28a
28c
28d
30
32
34
36
38a
38b
40
44

APPARATUS FOR SUPPLYING CORROSION INHIBITING MATERIAL TO INACCESSIBLE METAL SURFACES

BACKGROUND OF THE INVENTION

The present invention generally relates to apparatus for applying corrosion inhibiting material to inaccessible metal surfaces, such as the inner surface of a vehicle body panel.

It is known to provide apparatus for spraying a corrosion inhibiting material into the confines of a closed cavity having one or more injection openings, as evidenced by U.S. Pat. No. 4,108,382.

It is also known to provide apparatus permitting the slow release of corrosion inhibiting materials within a closed cavity, wherein a housing filled with such material is intended to be removably and threadably mounted in a cavity access opening, as evidenced by U.S. Pat. Nos. 2,766,069 and 3,871,823.

SUMMARY OF THE INVENTION

The present invention is directed towards an improved apparatus for applying slow release, corrosion inhibiting materials to inaccessible metal surfaces, and more particularly to an apparatus of this type, which is adapted for ease of initial installation and subsequent replacement of corrosion inhibiting material when an initial charge thereof has been depleted.

In accordance with the present invention there is provided in combination a cup-shaped retainer, which is intended to be permanently installed within a cavity by having the mounting rim portion thereof formed into clamping engagement with a panel peripherally of an access opening thereof through which the retainer is inserted for mounting purposes; a disposable cartridge for retaining a charge of corrosion inhibiting material and intended to be removably inserted within the retainer; a sealing disc or cover sized to engage an exterior surface of the body panel peripherally of the access opening; and a mounting screw removably threadably received by the retainer for purposes of effecting initial deformation of the mounting rim portion, releasably clamping the sealing disc against the body panel and for puncturing the cartridge to permit escape of contents therefrom.

DRAWINGS

The nature and mode of operation of the present invention will now be more fully described in the following detailed description taken with the accompanying drawings wherein.

DETAILED DESCRIPTION

Figure 1:
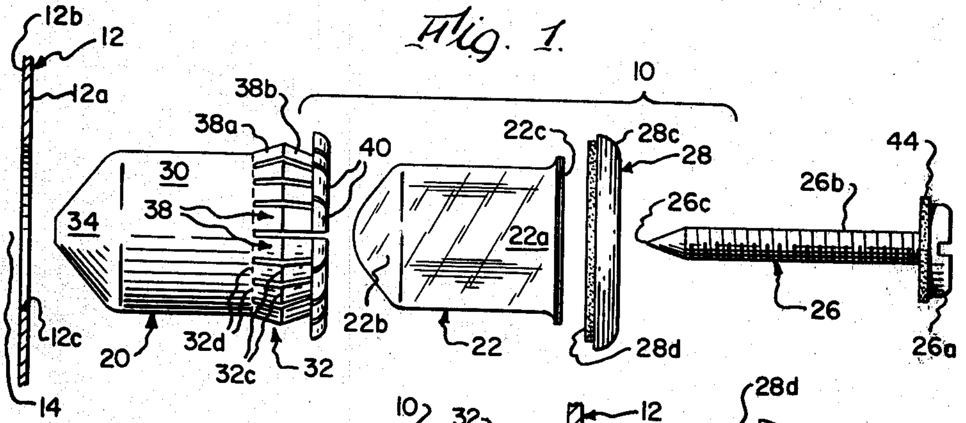
FIG. 1 is an exploded side elevational view of the apparatus of the present invention arranged in association with a vehicle body or door panel.

An apparatus for use in supplying a corrosion inhibiting material and formed in accordance with the present invention is generally designated as 10 in the drawings and shown in association with a vehicle body or door panel 12 having outer and inner surfaces 12*a* and 12*b*, respectively; and a through access opening or aperture

12*c* leading into a cavity 14 whose boundary surfaces, including for instance inner surface 12*b*, are intended to be protected against corrosion. As by way of example, access opening 12*c* may be a "plugged opening" of the type conventionally provided in vehicle body or door panels to facilitate injection of liquid rust proofing materials. Alternatively, in the absence of a preformed "plugged" opening, an opening may be suitably formed in the panel, as by a punching or drilling operation.

Apparatus 10 generally comprises a hollow retainer or mounting fixture 20; a throw away or replaceable cartridge 22 containing a charge of a suitable corrosion inhibiting material 24; a mounting screw 26; and a sealing disc or cover 28.

Retainer 20 is shown in the drawings as being of a generally cup-shaped configuration and provided with a generally cylindrical side wall 30 terminating at its free or outer end in a mounting rim portion generally designated as 32; and a base or end wall 34, which is joined to an opposite or inner end of the side wall and formed with a centrally located mounting aperture 36 sized to threadably receive mounting screw 26. Preferably, base wall 34 is conically shaped to facilitate guiding of screw 26 for insertion within aperture 36. Mounting rim portion 32 is defined by a plurality of fingers 38, which are formed integrally with and spaced apart annularly of side wall 30 and terminate in radially outwardly rolled retaining lips 40, which cooperate one with another to define a clamping rim extending peripherally of retainer 20. Deformation of fingers 38 in the manner to be described may be facilitated by preforming the fingers with a V-shaped configuration, wherein first and second finger halves or leg portions 38*a* and 38*b* are joined along fold or hinge lines 38*c*, and the first finger halves 38*a* are joined to side wall 30 along fold or hinge lines 38*d*. If desired, retaining lips 40 may be joined integrally to each other in order to define a continuous annular clamping rim, and in this case the fingers would be defined by a series of parallel slots extending between the clamping rim and side wall 30.

Figure 2:
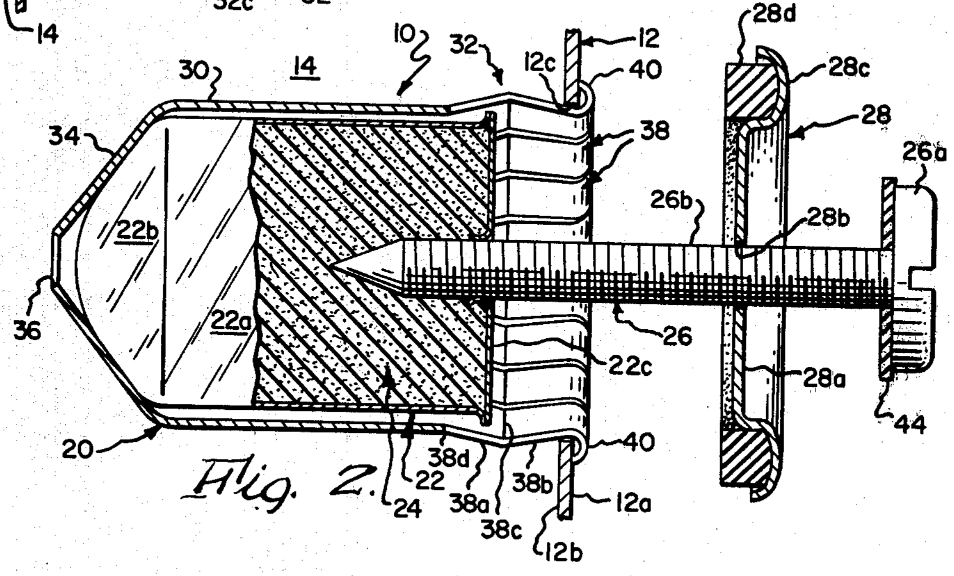
FIG. 2 is a sectional view showing the apparatus fitted within an access opening of the vehicle panel and in partly assembled condition.

Retainer 20 is sized to permit side wall 30 and fingers 38, when in their initial non-deformed state shown in FIGS. 1 and 2, to be inserted into cavity 14 through access opening 12*c* and position retaining lips 40 of the clamping rim in engagement with panel outer surface 12*a*. The clamping rim is considered to bound an inlet opening for permitting insertion of the cartridge into retainer 20, whereas the openings or slots between adjacent fingers 38 are considered to define discharge or outlet openings for corrosive inhibiting material.

Figure 3:
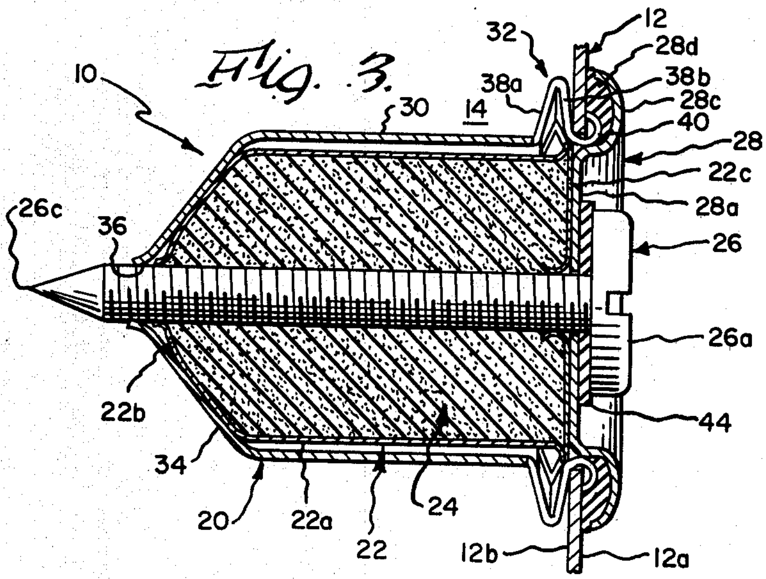
FIG. 3 is a view similar to FIG. 2, but with the apparatus shown in its fully assembled condition.

Cartridge 22 is best shown in FIGS. 2 and 3 as including a generally cup-shaped body having side and end walls 22*a* and 22*b*, respectively; and a cover plate 22*c*, which has its periphery suitably fixed to the outer or free end of side wall 22*a* in order to define an opposite end wall for the cartridge and seal charge 24 within the cartridge. The configuration of cartridge 22 generally conforms to that of retainer 20 with cartridge side wall 22*a* being of a diameter facilitating the removal/insertion of the cartridge within the retainer. The axial length of cartridge 22 is preferably such that it may be positionally clamped between retainer end wall 34 and the inner surface of sealing disc 28, when the apparatus is in its assembled condition shown in FIG. 3 in order to prevent rattling of the cartridge within the retainer during use of a vehicle. Cartridge 22 may be fabricated from any desired material providing for required shelf/storage life of the material forming charge 24, while at the same time permitting bottom wall 22b and plate 22c to be readily punctured by mounting screw 26, during the assembly operation. Charge 24 may be in solid cake or particle form or in liquid form, as desired, and be formed from any known composition having corrosion inhibiting properties. As by way of example, reference is made to the disclosures of U.S. Pat. Nos. 2,577,219; 2,592,451; 2,766,069 and 3,871,823, whose disclosures of corrosion inhibiting materials are incorporated by reference.

Mounting screw 26 is shown in the drawings as having an enlarged, slotted head portion 26a and a threaded shank portion 26b terminating at its free end in a sharp point or tip 26c. A resiliently deformable sealing ring 44 is applied over shank portion 26b and positioned adjacent head portion 26a for purposes of fluid sealing the latter relative to sealing disc 28.

Again making reference particularly to FIGS. 2 and 3, it will be understood that sealing disc 28 is characterized as having a flat central portion 28a, which is preferably sized to be received within retainer 20 for engagement with cartridge 22 upon assembly of apparatus 10 and formed with an aperture 28b for freely receiving screw shank portion 26b; and an upstanding, annular rim portion 28c, which is recessed to receive a resiliently deformable sealing ring 28d.

Apparatus 10 may be assembled and initially installed by first inserting retainer 20 through access opening 12c and into cavity 14 sufficiently to place retaining lips 40 against panel outer surface 12a. Preferably, screw 26 would then be inserted through aperture 28b of sealing disc 28 and threaded into aperture 36 of retainer 20 sufficiently to first draw sealing ring 28d into engagement with panel outer surface 12a and then effect deformation of fingers 38 until finger halves 38b are forced into clamping engagement with panel inner surface 12b, whereafter finger halves 38b and lips 40 cooperate to clamp panel 12 peripherally of access opening 12c and lock retainer 20 in assembled condition. Thereafter, screw 26 would be unthreaded relative to aperture 36; cartridge 22 inserted within retainer 20; the screw forced axially through cartridge 22 for successively puncturing plate 22c and end wall 22b; and the screw again threaded into aperture 36 until sealing ring 28b is again seated against panel outer surface 12a and disc central portion 28a is disposed in clamping engagement with cartridge cover plate 22c, thereby completing assembly of the apparatus in the manner indicated in FIG. 3. After assembly of apparatus 10 the escape of any portion of charge 24 outwardly through aperture 12c is prevented due to the fluid seal created between panel outer surface 12a and sealing disc 28 by sealing ring 28d or through sealing disc aperture 28b by the seal created between the sealing disc and screw head portion 26b by sealing ring 44.

After assembly of apparatus 10 has been completed, corrosion inhibiting material is free to leak or escape through the apertures in cartridge 22 created by insertion of screw 26 and then pass through the discharge openings defined by the openings between adjacent fingers 38 for application directly to panel inner wall 12b in the case of a liquid or for dispersion uniformly within cavity 14 in the case of a gas. In either case, movement of corrosion inhibiting material between the apertured ends of cartridge 22 and the openings between adjacent fingers 38 may be facilitated, if required, by forming ribs or channel recesses, not shown, in the facing surfaces of end walls 22b and 34 and/or in the facing surfaces of cover plate 22c and sealing disc central portion 28a. Alternately, if desired, escape of corrosion inhibiting material from within cartridge 22 may be effected or facilitated by forming one or more apertures, not shown, in cartridge side wall 22a; such apertures being normally fluid sealed until immediately prior to installation of the cartridge within retainer 22 by means of a peel-off or perforated sealing tape or the like.

As an alternative to the above described preferred assembly procedure, it would of course be possible to simultaneously assembly all elements of the assembly in the manner generally suggested by FIG. 2 of the drawings.

After depletion of the charge of corrosion inhibiting material from the first installed cartridge, a new or fresh cartridge may be installed by the simple procedure of unthreading screw 26 from within aperture 36, removing the depleted cartridge from the screw, forcing the screw through a fresh cartridge and again threading the screw into aperture 36 until sealing disc 28 is returned for sealing engagement with panel outer surface 12a.

As will be apparent, the size and/or composition of charge 24 will determine the useful life of each cartridge.

While I have shown and described a specific embodiment of my invention, further modifications and improvements will likely occur to those skilled in the art. Therefore, I desire that this invention not be limited to the particular form shown and I intend in the appended claims to cover all modifications which do not depart from the spirit and scope of this invention.

What is claimed is:

1. An apparatus for applying corrosive inhibiting material to inaccessible metal surfaces via an access opening formed in a panel having outer and inner surfaces, said apparatus comprising in combination;
   - a cup-shaped retainer having a discharge opening and a mounting rim portion, said retainer being inserted inwardly through said access opening to position said discharge opening inwardly beyond said inner surface and said mounting rim portion being fixed to said panel peripherally of said access opening;
   - a disposable cartridge for containing a charge of corrosive inhibiting material and sized to be removably inserted within said retainer;
   - a sealing disc sized to engage said outer surface of said panel peripherally of said access opening; and
   - a mounting screw removably threadably received by said retainer for releasably clamping said sealing disc against said outer surface of said panel and for puncturing said cartridge to permit escape of contents therefrom into said retainer and outwardly thereof through said discharge opening.

2. An apparatus for applying corrosive inhibiting material to inaccessible metal surfaces rendered accessible by an access opening formed in the panel having outer and inner surfaces, said apparatus comprising in combination:
   - a cup-shaped retainer having a discharge opening and a mounting rim portion deformable for clampingly engaging with said panel peripherally of said access opening to positionally fix said retainer relative to said panel and to locate said discharge opening inwardly of said panel beyond said inner surface;

a disposable cartridge for retaining a charge of corrosive inhibiting material and sized to be removably inserted within said retainer;

a sealing disc sized to engage said outer surface of said panel peripherally of said access opening; and a mounting screw removably threadably received by said retainer for effecting deformation of said mounting rim portion into clamping engagement with said panel, for releasably clamping said sealing disc against said outer surface of said panel and for puncturing said cartridge to permit escape of said corrosion inhibiting material therefrom into said retainer for discharge through said discharge opening.

3. An apparatus according to claim 2, wherein said retainer includes a generally conically shaped base wall having a centrally located aperture threaded to receive said screw, said cartridge is formed with opposite end walls with a first end wall thereof being of generally conically shaped configuration, and said screw is insertable through said opposite end walls of said cartridge and operable for clamping said sealing disc against a second of said end walls of said cartridge to releasably maintain said first end wall of said cartridge against said base wall of said retainer incident to the clamping of said sealing disc against said outer surface of said panel.

4. An apparatus according to claim 3, wherein said sealing disc has a central portion arranged for engagement with said second of said end walls of said cartridge and an upstanding annular rim portion recessed to receive a resiliently deformable sealing ring arranged for engagement with said outer surface of said panel, said central portion of said sealing disc being apertured to removably receive a shank portion of said screw and there is additionally provided a sealing ring surrounding said shank portion of said screw for providing a fluid seal between a head portion of said screw and said central portion of said sealing disc.

5. An apparatus according to claim 2, 3, or 4 wherein said retainer additionally includes a generally cylindrical side wall, said mounting rim portion includes a plurality of fingers spaced apart annularly of said side wall of said retainer and a clamping rim, said fingers having first ends thereof formed integrally with said side wall and second ends thereof formed integrally with said clamping rim, said clamping rim extending annularly of said retainer and sized for abutting engagement with said outer surface of said panel incident to insertion of said side wall of said retainer inwardly through said access opening, said fingers being deformable for engagement with said inner surface of said panel and cooperating with said clamping rim to fix said retainer to said panel, and the spacings between said fingers define a plurality of discharge openings.

6. An apparatus according to claim 2, wherein said retainer additionally includes a base wall defining a centrally located aperture for threadably receiving said screw and a generally cylindrical side wall, said mounting rim portion includes a plurality of fingers spaced apart annularly of said side wall and a clamping rim, said fingers having first ends thereof formed integrally of said side wall and second ends thereof form integrally with said clamping rim, said clamping rim extending annularly of said retainer and sized for abutting engagement with said outer surface of said panel peripherally of said access opening, said fingers being deformable for engagement with said inner surface of said panel peripherally of said access opening and cooperating with said clamping rim to fix said retainer to said panel, the spacings between said fingers defining a plurality of discharge openings, said cartridge having opposite end walls, and said screw is insertable through said opposite end walls of said cartridge to effect puncturing of said cartridge and for receipt within said aperture.

7. An apparatus according to claim 6, wherein said sealing disc includes a central portion having a through aperture for removably receiving a threaded shank portion of said screw and an upstanding annular rim portion recessed to receive a resiliently deformable sealing ring, said central portion and said base wall engaging with said opposite ends to positionally locate said cartridge within said retainer, said sealing ring being sized to engage with said clamping rim and said outer surface of said panel radially outwardly of said clamping rim, and there is provided an additional sealing ring disposed about said shank portion intermediate said control portion of said sealing disc and a head portion of said screw for providing a fluid seal for said aperture of said central portion.

* * * * *